(12) United States Patent
Price

(10) Patent No.: US 8,722,943 B1
(45) Date of Patent: May 13, 2014

(54) CARBOHYDRATE AND POLYOL ETHERS AS RENEWABLE OILS, GREASES, AND LIQUID FUELS

(75) Inventor: Neil P. Price, Edelstein, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/478,250

(22) Filed: May 23, 2012

(51) Int. Cl.
*C07C 41/09* (2006.01)
*C07C 41/28* (2006.01)
*C07C 43/13* (2006.01)

(52) U.S. Cl.
CPC .............. *C07C 41/09* (2013.01); *C07C 41/28* (2013.01); *C07C 43/135* (2013.01)
USPC ........................................................ 568/679

(58) Field of Classification Search
CPC ........ C07C 43/135; C07C 41/09; C07C 41/28
USPC ........................................................ 568/679
See application file for complete search history.

(56) References Cited

U.S. PATENT DOCUMENTS 4,659,846 A * 4/1987 Maurer et al. ................. 549/464
5,869,702 A * 2/1999 Nakagawa et al. ........... 549/364

FOREIGN PATENT DOCUMENTS

BR          200700063      *  9/2008

OTHER PUBLICATIONS

Streitwieser, Jr., Andrew, et al., Macmillan Publishing Co, Inc., 1976, "Introduction to Organic Chemistry", pp. 235-237.
Dermer, Otis C., "Metallic Salts of Alcohols and Alcohol Analogs", Reviewed Jan. 1, 1934, pp. 385-420.

* cited by examiner

*Primary Examiner* — Rosalynd Keys
(74) *Attorney, Agent, or Firm* — John Fado; Randall E. Deck; Albert Y. Tsui

(57) ABSTRACT

Alkyl ethers are produced directly from polyols or their salts in a single step reaction, or alternatively, the polyols are first converted to a ketal or acetal derivative which comprises at least one free hydroxyl moiety and one or more ketal or acetal moieties. In either embodiment, the polyol, its salt, or its ketal or acetal derivative is reacted with an alkylating agent to produce a first alkoxy polyol ether comprising one or more alkoxy moieties formed at the sites of the free hydroxyl moieties. Ethers prepared from the polyol ketal or acetal derivatives retain their ketal or acetal moieties, which may be hydrolyzed to additional free hydroxyls and reacted with alkylating agent to produce a second alkoxy polyol ether. Alkyl tosylates are preferred alkylating agents. The spent alkylating agents may also be recovered and regenerated. Recovered alkoxy polyol ethers may be used as renewable fuels, solvents and lubricants.

30 Claims, 3 Drawing Sheets

US 8,722,943 B1

CARBOHYDRATE AND POLYOL ETHERS AS RENEWABLE OILS, GREASES, AND LIQUID FUELS

BACKGROUND OF THE INVENTION

1. Field of the Invention

The invention is drawn to a method for the production of ethers from polyols, catalysts for use in producing the ethers, and the use of the ethers as renewable fuels.

2. Description of the Prior Art

Existing techniques for the preparation of ethers are variants of the classic Williamson ether synthesis, and generally require dangerously volatile and highly carcinogenic alkylating agents such as methyl iodide or dimethyl sulfate. Moreover, the reactions also typically require a non-aqueous and expensive co-solvent, such as DMSO or dimethylformamide.

Many simple ethers (such as diethylether) are known compounds, and are volatile, flammable solvents. Diethylether, for example, is used in cellulose acetate production and as a starter fluid for small gasoline engines. Other synthetic ethers include cyclic furans: tetrahydrofuran (THF) and 1,4-dioxane are produced commercially as solvents. In 1990, US production of dioxane was between 10.5 and 18.3 million pounds. About 200,000 tons of THF are produced annually, mainly as an industrial solvent for PVC and in varnishes.

In addition to the market for known ethers, there is a clear future need for renewable materials and chemicals to replace those from dwindling petroleum feedstocks, and biobased products from biorefinery carbohydrates are a high priority. The energy potential to supplement gasoline and diesel usage in the U.S. alone is huge, currently approximately 15 and $6 \times 10^{10}$ gal/year, respectively. In addition to fuels, which despite their high volume are relatively low value products, other materials are required to replace lubricant oils and greases, emulsifiable oils, and various substitute solvents, including kerosene. As of 2010, glycerol, sorbitol, and xylitol/arabinitol are all in the DOE "top 10" chemical opportunities from carbohydrates (Bozell and Petersen. 2010. Technology development for the production of biobased products from biorefinery carbohydrates—the US Department of Energy's "Top 10" revisited. Green Chem. 12:539-554). In fact, crude glycerol from biodiesel production accounts for ~1 million tons/year, with projected prices as low as $0.11/kg. Thus, the need remains for improved technologies for the production of ethers, and for the production of renewable fuels and other products from existing agriculture-based substrates.

SUMMARY OF THE INVENTION

I have now discovered a novel process for converting polyols into their corresponding alkyl ethers. The ethers may be produced directly from polyols or their salts in a single step reaction, or in the alternative, the polyols may be first converted to a ketal or acetal derivative which comprises at least one free hydroxyl moiety and one or more ketal or acetal moieties (effectively protecting at least two of the hydroxyl moieties from initial reaction). In either embodiment, the polyol, its salt or its ketal or acetal derivative is reacted with a first alkylating agent under conditions effective for alkylation of one or more of the hydroxyl moieties of the polyol or its derivative to produce a first alkoxy polyol ether. The resulting first alkoxy polyol ether may be recovered for subsequent use, particularly when prepared directly from the polyol or its salts. However, when reacting the polyol ketal or acetal derivatives, the ketal or acetal moieties are protected from reacting with the alkylating agent. The remaining ketal or acetal moieties of this first alkoxy polyol ether may then be hydrolyzed to additional free hydroxyl moieties, and this resulting polyol may be subsequently reacted with a second alkylating agent under conditions effective for alkylation of the remaining free hydroxyl moieties to produce a second alkoxy polyol ether. This alternative embodiment allows the incorporation of different alkyl moieties into the ether by using a different alkylating agent in the second alkylation reaction. Although a variety of alkylating agents may be used, in a preferred embodiment a novel alkyl tosylate is used as one or both of the first and second alkylating agents. In another optional, yet preferred embodiment, the spent alkylating agents may be recovered, and subsequently regenerated and recycled for repeated use. The alkoxy polyol ethers produced may be recovered for use as renewable fuels, solvents, and lubricants, including oils and greases.

In accordance with this discovery, it is an object of this invention to provide a new process for producing ethers from polyols, particularly renewable, agriculture-based polyols.

It is another object of this invention to provide a process for producing ethers from polyols in high yields.

Another object of this invention to provide a process for producing ethers from polyols with improved safety, utilizing non-volatile alkylating agents.

A further object of this invention to provide a process for producing ethers from polyols in an aqueous solvent, and wherein the product ethers may be readily recovered from the reaction mixture.

Yet another object of this invention to provide a process for producing ethers from polyols wherein spent alkylating agent may be readily recovered, regenerated and reused.

Still another object of this invention to provide a process for producing ethers from polyols utilizing a solid phase alkylating agent which may be easily separated from the reaction mixture.

Still another object of this invention is to provide novel alkylating agents for use in the reaction to produce ethers from polyols.

Still another object of this invention is to provide ethers from renewable, agriculture-based polyols, which ethers may be used as fuels, solvents and lubricants, including oils and greases.

Other objects and advantages of this invention will become readily apparent from the ensuing description.

BRIEF DESCRIPTION OF THE FIGURES

FIG. 1A shows the production of glycerol by existing biodiesel processes. FIG. 1B shows the recyclable process for the formation of sugar/polyol (glycerol) ethers using aqueous alkylating reagents in accordance with a first embodiment.

DETAILED DESCRIPTION OF THE INVENTION

Figure 1:
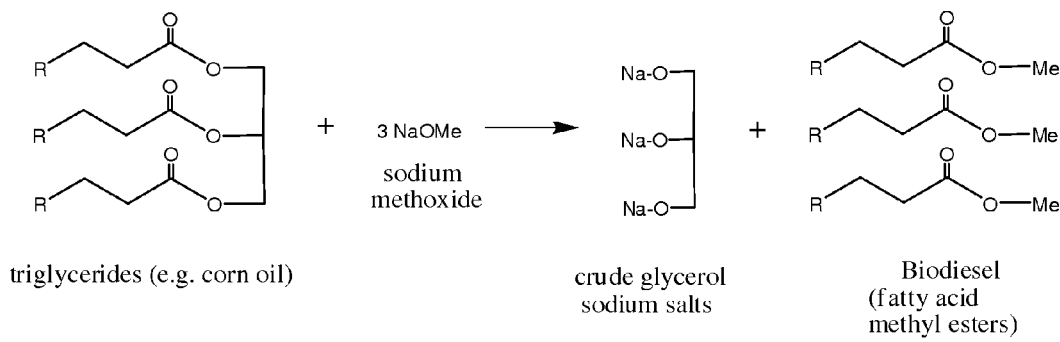
FIG. 1 illustrates one example for the potential use of the invention for the "drop-in" recovery of ethers from glycerol produced via existing biodiesel techniques.
Figure 1:
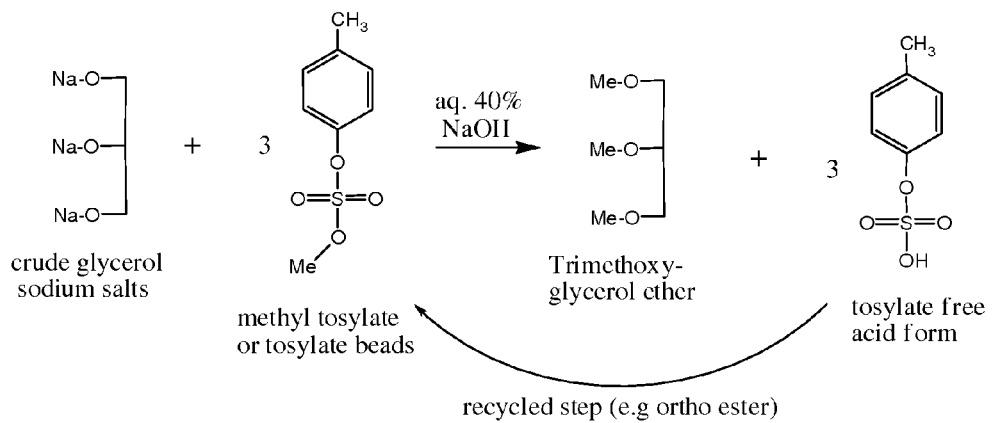

The process described herein may be used to produce alkoxy polyol ethers from a variety of polyols, including those of plant, animal, microbial or synthetic origin, and particular agriculture-based sugars and polyols. Suitable polyols for use herein are defined to include any C3 to C7 hydrocarbon having two or more hydroxyl moieties, not to include aldoses or ketoses. The hydrocarbon may be straight or branched chains or cyclic, and are typically saturated, although it is envisioned that unsaturated hydrocarbons may be used as well. Thus, without being limited thereto, suitable polyols include diols, glycerols (having three hydroxyl groups) and sugar alcohols, although glycerol is preferred because of its low cost. Glycerol for use herein may be obtained from a variety of commercial sources, and for reactions requiring a high degree of purity, the glycerol may be readily obtained in pure or substantially pure form. However, in a preferred embodiment the glycerol is obtained as the co-product from the preparation of biodiesel fuel from vegetable, algal, microbial or animal oils. Moreover, because the reaction is an aqueous solvent, the crude glycerol co-product containing water may be used directly without purification. A variety of other polyols are also suitable for use herein, particularly sugar alcohols, which may be cyclic or acyclic. Acyclic sugar alcohols, which include alditols, have the general formula $CH_2OH(CHOH)_nCH_2OH$ wherein n is 2 or greater, preferably from 2 to 5. Examples of sugar alcohols include, but are not limited to, sorbitol (glucitol), maltitol, mannitol, inositol, dulcitol, fucitol, iditol, xylitol, arabitol, ribitol, erythritol and threitol. Alditols may be obtained from commercial sources or prepared by catalytic hydrogenation of aldose sugars over a Ni catalyst as is known in the art. Examples of diols which may be used include but are not limited to propanediol and n- or t-butanediol.

The reaction may be practiced using polyols which have not been modified, or the reaction may be practiced using salts or ketal or acetal derivatives of the polyols. Use of ketal or acetal derivatives in the multi-step production of the ethers surprisingly may provide greater yields of the ethers than the single step reaction of the polyols per se, and also enables the practitioner to produce ethers having different alkoxy groups, as will be demonstrated below. A variety of salts of polyols may be used, including but not limited to Na, K or Ca salts, although Na salts such as the Na salt of glycerol recovered from biodiesel fuel production are preferred. Acetal or ketal derivatives of any of above-described polyols may be prepared using known techniques, such as by acid-catalyzed reaction with any ketone or aldehyde. Suitable aldehydes and ketones for use in this reaction may be of the formula $R_1CHO$ or $R_1COR_2$, respectively, wherein $R_1$ and $R_2$ are hydrocarbons, with acetone, acetaldehyde, formaldehyde and benzaldehyde being preferred. A variety of acid catalysts may also be used, including dehydrating acids such as sulfuric acid or solid cationic or acidic exchange resins, although the resins are preferred for ease of separation from the reaction medium. Thus, acetal or ketal polyol derivatives for use herein may be shown by the formula:

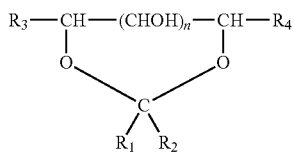

wherein $R_1$ and $R_2$ are as described above, $R_3$ is —OH or —$(CHOH)_m$—$CH_2OH$, $R_4$ is —OH or —$(CHOH)_p$—$CH_2OH$, n is 0 or 1, and m and p are independently selected from an integer from 0 to 5, with the proviso that the sum of n+m+p is 1 to 5.

The reaction of the polyol, its salt or its ketal or acetal derivative with alkylating agent is conducted under conditions effective for alkylation of one or more of the hydroxyl moieties of the polyol or its derivatives to produce a first alkoxy polyol ether (i.e., comprising one or more alkoxy moieties formed at the sites of the free hydroxyl moieties). Alkylating agents which are suitable for use herein, include alkyl sulfonated resins (a strong acid cation exchange resin) and alkyl tosylates (also referred to as alkylated tosyl sulfonic acid, described in greater detail below), with alkyl tosylates being preferred. A variety of sulfonated resins are commercially available, including but not limited to, cross-linked polystyrene sulfonic resins such as the strong acid cation exchange Dowex or Amberlyst resins (both available from Dow Chemical Co., Midland, Mich.). Preferred alkyl moieties for the sulfonated resins or alkyl tosylates include methyl, ethyl, propyl, and n- or t-butyl, with methyl and ethyl being preferred. It is also understood that a combination of different alkylating agents (having different alkyl groups) may also be used. The reaction is conducted with mixing under strongly alkaline, aqueous conditions, preferably at a pH of approximately 13-14. The particular base used is not critical, although KOH, CaOH and particularly NaOH are preferred. 20-50% aqueous solutions of the base are typical, with 30-40% preferred. The temperature of the reaction also is not critical, and the reaction will even proceed at room temperature, although the reaction time is considerably longer with lower temperatures. Reaction at reflux temperature is therefore preferred. Depending upon the particular polyol used, a small amount, up to 30% (by volume), of an optional non-polar co-solvent such as acetone or acetonitrile may be added to facilitate formation of a stable emulsion of the reactants and prevent precipitation of the base. The reaction time will vary with the temperature, but at 100° C. typically reaches completion in approximately 3 hours.

Depending upon the starting polyol or derivative reacted, upon completion of the reaction the first alkoxy polyol ether may be recovered or further reacted. When using the polyol or its salt as the starting reactant, most of the first alkoxy polyol ether molecules are typically fully alkylated (i.e., all of the free hydroxyl moieties have been alkylated) and produced in relatively high yields. For instance, the first polyol ether produced by reaction of glycerol or glycerol salts comprise as a major component tri-alkoxy glycerol ethers, with relatively small amounts of di-alkoxy ethers also present. Because the alkoxy polyol ethers tend to be more volatile and hydrophobic than their polyol starting materials, they readily form separate phase layers from the polyol which remains in the aqueous phase. Thus, the alkoxy polyol ethers may be recovered by distillation, decantation or extraction. In contrast, when the starting reactant is a ketal or acetal derivative of the polyol, the first alkoxy polyol ether comprises one or more ketal or acetal moieties (which do not react) and at least one alkoxy moiety (formed at the sites of any free hydroxyl moieties). Thus, the first alkoxy polyol ether is further reacted to hydrolyze these ketal or acetal moieties to form a stable intermediate alkoxy polyol ether having additional free hydroxyl moieties (whereas the alkoxy moieties are stable and are not hydrolyzed). This hydrolysis is acid catalyzed, and may be readily conducted by addition of any aqueous acidic solution, preferably at a pH of approximately 1 to 2. Upon completion of the hydrolysis of the acetal or ketals, the resultant intermediate polyol ether is reacted with a second alkylating agent under conditions effective for alkylation of one or more of the free hydroxyl moieties to produce a second alkoxy polyol ether (comprising alkoxy moieties at the sites of the free hydroxyl moieties). The second alkylating agent may be the same as or different from the first, and the conditions for this alkylation reaction are the same as described for the initial alkylation of the starting polyol. Use of a different alkylating agent allows the user to incorporate different alkyl moieties into the ether. Moreover, I have discovered that use of this multi-step alkylation reaction starting with ketal or acetal derivatives of the polyols may produce higher yields than the single step alkylation of the polyols or their salts. Upon completion of this second alkylation, the second alkoxy polyol ether may be recovered as described above.

In accordance with a preferred embodiment, the spent alkylating agents from either or both of the alkylation steps may be recovered and regenerated for re-use in subsequent reactions. Recovery is facilitated by use of alkylating agents immobilized on solid phase supports such as beads or resins, which may be readily recovered by filtration or settling. In the embodiment using soluble alkylating agents, the spent tosylate is sodium tosylate [p-toluenesulfonic acid sodium salt] which remains in the aqueous layer. This spent tosylate may then be recovered for regeneration by evaporation to dryness.

Alkylating agents for use in the reaction are prepared by alkylation of the corresponding sulfonated acid resins such as the above-mentioned Dowex or Amberlyte resins, or the preferred p-toluenesulfonic acid. The sulfonated resin or p-toluenesulfonic acid are reacted with an orthoester of the desired alkyl group, which alkyl orthoester may be represented by the general formula R'C(OR)$_3$ wherein R is an C1 to C4 alkyl group, including methyl, ethyl, propyl, and n- or t-butyl, with methyl and ethyl alkyl groups being preferred (i.e., trimethyl- or triethyl-orthoacetate). This alkyl orthoester may be prepared using known techniques, such as by the acid catalyzed reaction of a nitrile R'CN with the alkyl alcohol ROH. The reaction of the sulfonated resin or p-toluenesulfonic acid with the alkyl orthoester is typically conducted at reflux temperature, and the reaction proceeds relatively quickly, reaching 100% yields in as little as 30 minutes (e.g. Dowex 50 W resin 2 g; trimethyl orthoacetate 4.2 mL, 4.4 eq.; no solvent needed; stir at room temperature for 30 mins; filter to recover resin. Wash resin with acetone, and air dry). The general structure of the alkyl tosylate produced herein and subsequently used in the alkylation of the polyols is of the formula:

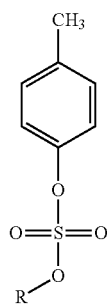

wherein R is as described above. Regeneration (or re-alkylation) of the spent alkylation reagents recovered following the reaction with the polyol may be conducted in the same manner.

In an optional yet particularly preferred embodiment, the alkylation agents are provided as an immobilized solid phase substrate. Solid phase alkylation agents are preferred for ease of separation and recovery following completion of the reaction with the polyols, such as by filtration or settling. Solid phase cross-linked polystyrene sulfonic resins are commercially available from a variety of sources, such as Dowex 50W or Amberlyst 15 resins (both available from Dow Chemical Co., Midland, Mich.). Because these Dowex resin beads share the same tosylate moiety —C$_6$H$_4$SO$_3$⁻ moiety, the solid phase tosylates may be prepared therefrom. These solid phase materials may be alkylated by direct reaction with alkyl orthoester as described above to produce the desired solid phase alkylation agents for reaction with the polyols.

The alkoxy polyol ethers produced by the alkylation reactions may be used as fuels, solvents, and lubricants, including oils and greases. As noted above, the ethers are more volatile and hydrophobic than their corresponding polyols, and unlike esters, the ethers are chemically and thermally stable, rendering the ethers as attractive renewable alternatives for fuels, solvents and lubricants. For example, trimethylglycerol ether has a calculated boiling point of 131° C. and melting point of −65° C., which compares well with isooctane (B.pt. 106/ M.pt. −107° C.) or with the major alkane component of gasoline, n-octane (B.pt. 110/M.pt. −94° C.). Monomethyl- and dimethyl-glycerol ethers have higher B.pts (244 and 177° C., respectively), and higher polyol ethers such as pentamethylxylitol or hexamethylsorbitol are oils (calc. M.pts −5 and 25° C., respectively). Ethers produced from smaller polyols, such as xylitol, arabitol and preferably glycerol, and most preferably their methoxy or ethoxy ethers, are particularly suitable for replacing at least a portion of the combustible components of conventional fuels, such as kerosene or gasoline. Thus, the ethers may be used as fuels for a variety of internal combustion engines, including reciprocating engines (including piston engines such as a two-stroke engine, four stroke engine and diesel engine), rotary engines, gas turbines, and jet engines (including but not limited to a turbojet, turbofan, ramjet and rocket). These ethers produced from smaller polyols may also be used as solvents, particularly for paints and plastics. Ethers produced from larger polyols, particularly those having 6 or more carbons, are generally less volatile and behave like conventional greases, waxes and heavy oils, and thus are particularly suited for use as lubricants.

Where the final use is as a fuel, the alkoxy poly ethers may be formulated with conventional fuel components, including but not limited to kerosene, naphtha, gasoline, polyalkylfluoride lubricants, antioxidants, antistatic agents, corrosion inhibitors, icing inhibitors, and biocides. For lubricant applications, it is contemplated that other additives may be formulated with the ethers. Illustrative of these additives are detergents, antiwear agents, antioxidants, viscosity index adjusters, pour point depressants, corrosion protectors, friction coefficient modifiers, colorants and the like as well-known in the art.

The following examples are intended only to further illustrate the invention and are not intended to limit the scope of the invention as defined by the claims.

Example 1

Figure 3:
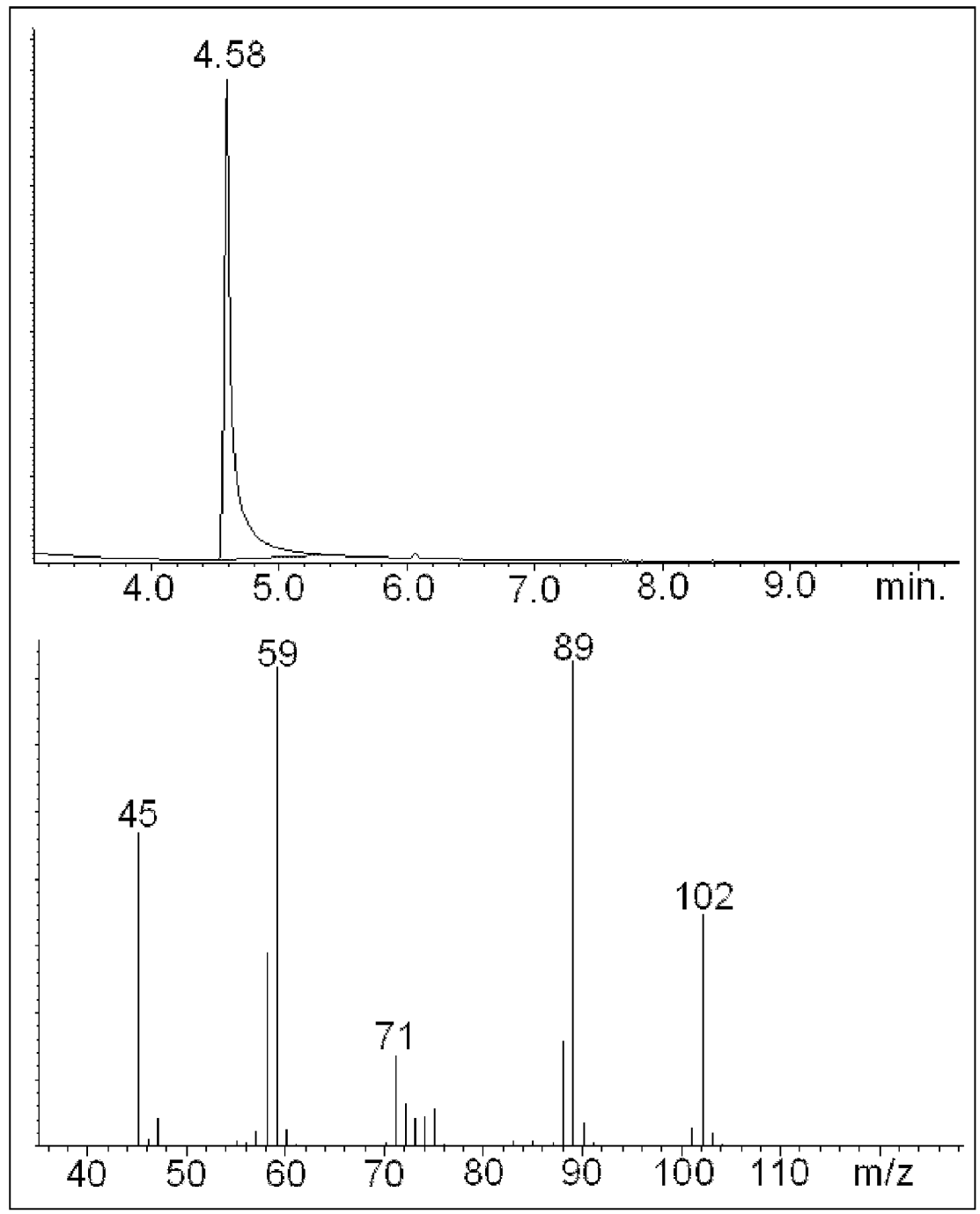
FIG. 3 shows the gas chromatograph (top) and mass spectrum (bottom) for the trimethyl glycerol ether (TMG-E) prepared as described Example 1.

Methyl tosylate alkylation agent was prepared p-toluenesulfonic acid with trimethyl orthoester at room temperature. The reaction was complete in 30 minutes with 100% yield. 12.8 g of methyl tosylate was reacted with 2.0 g glycerol in aqueous NaOH 8 mL 40% aq. NaOH) in a small scale vessel for 3 hours at 100° C. Trimethoxy glycerol ether (TMG-E) was obtained in near quantitative yield as a volatile clear solvent. The gas chromatograph (top) and mass spectrum (bottom) for the trimethoxy glycerol ether is shown in FIG. 3.

Example 2

Figure 2:
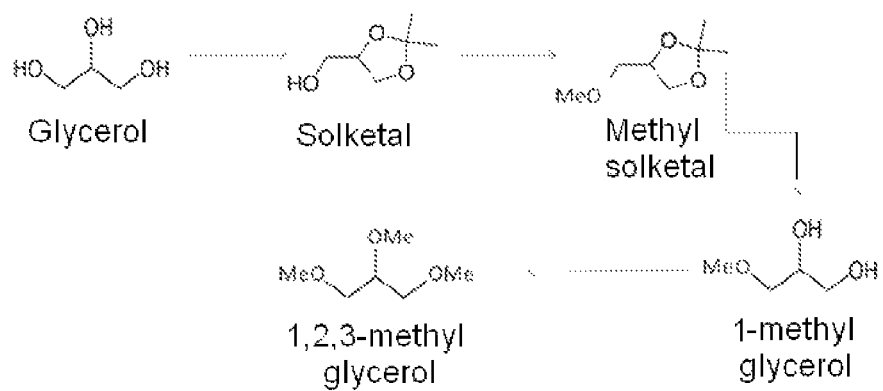
FIG. 2 shows an example of the recyclable process for the formation of sugar/polyol (glycerol) ethers in accordance with a second embodiment a described in Example 2.

Trimethyl glycerol was prepared from glycerol through a ketal glecerol derivative, solketal (1,2-isopropylidene glycerol) as shown in FIG. 2. Solketal starting material was prepared by reacting 1 g glycerol with 2 ml acetone and 1 g Dowex 50W strong cation exchange resin (Dow Chemical Co., Midland, Mich.) at 60° C. for 1 hour. The resultant solketal (3 mmol) was reacted with 3 mmol methyl tosylate (as prepared in Example 1) in 3 mmol NaOH with mL water in a small scale vessel for 2 hours at 70° C., producing methyl solketal. Hydrolysis of the methyl solketal was effected by reaction with Dowex 50W strong cation exchange resin (½") in 4 ml methanol for 2 hours at 70° C., producing 1-methyl glycerol. The 1-methyl glycerol produced from the hydrolysis was reacted with 2 molar equivalents of methyl tosylate in aqueous NaOH for 2 hours at 70° C., yielding 1,2,3-trimethoxy glycerol ether.

It is understood that the foregoing detailed description is given merely by way of illustration and that modifications and variations may be made therein without departing from the spirit and scope of the invention.

I claim:

1. A method for producing alkoxy polyol ethers comprising providing a polyol or polyol derivative comprising a salt of a polyol or a ketal or acetal of a polyol which comprises at least one free hydroxyl moiety and one or more ketal or acetal moieties, reacting said polyol or polyol derivative with a first alkylating agent under conditions effective for alkylation of one or more hydroxyl moieties of said polyol or polyol derivative to produce a first alkoxy polyol ether comprising one or more alkoxy moieties and spent first alkylating agent, recovering said spent first alkylating agent, and regenerating said spent first alkylating agent, wherein said regenerating comprises reacting said spent first alkylating agent with an alkyl orthoester and said first alkylating agent comprises a first alkyl tosylate.

2. The method of claim 1 wherein said providing and reacting comprise said polyol or said salt of a polyol, and said method further comprises recovering said first alkoxy polyol ether.

3. The method of claim 2 wherein said polyol or said salt of a polyol comprises glycerol, a sugar alcohol or mixtures thereof.

4. The method of claim 3 wherein said polyol or said salt of a polyol comprises glycerol and said alkyl tosylate comprises methyl tosylate, ethyl tosylate or combinations thereof.

5. The method of claim 1 wherein said polyol or said salt of a polyol and said first alkylating agent are reacted in an aqueous solvent.

6. The method of claim 1 wherein said providing and reacting comprise said ketal or acetal of said polyol, and said first alkoxy polyol ether comprises said one or more ketal or acetal moieties and at least one said alkoxy moiety.

7. The method of claim 6 further comprising reacting said first alkoxy polyol ether to hydrolyze said ketal or acetal moieties to additional free hydroxyl moieties, further reacting with a second alkylating agent under conditions effective for alkylation of one or more of the free hydroxyl moieties to produce a second alkoxy polyol ether, and recovering said second alkoxy polyol ether, wherein said second alkylating agent comprises a second alkyl tosylate.

8. The method of claim 7 wherein said first alkyl tosylate is different from said second alkyl tosylate.

9. The method of claim 7 wherein said ketal or acetal of said polyol comprises glycerol, a sugar alcohol or mixtures thereof.

10. The method of claim 9 wherein said ketal or acetal of said polyol comprises glycerol and said first alkyl tosylate and said second alkyl tosylate are independently selected from the group consisting of methyl tosylate and ethyl tosylate.

11. The method of claim 7 wherein said ketal or acetal of said polyol and said first alkylating agent are reacted in an aqueous solvent.

12. A method for producing alkoxy polyol ethers comprising providing a polyol or polyol derivative comprising a salt of a polyol or a ketal or acetal of a polyol which comprises at least one free hydroxyl moiety and one or more ketal or acetal moieties, reacting said polyol or polyol derivative with a first alkylating agent under conditions effective for alkylation of one or more hydroxyl moieties of said polyol or polyol derivative to produce a first alkoxy polyol ether comprising one or more alkoxy moieties and spent first alkylating agent, recovering said spent first alkylating agent and regenerating said spent first alkylating agent, wherein said first alkylating agent is immobilized on a solid phase support.

13. The method of claim 12 wherein said first alkylating agent comprises a first alkyl tosylate immobilized on said solid phase support.

14. The method of claim 12 wherein said providing and reacting comprise said polyol or said salt of a polyol, and said method further comprises recovering said first alkoxy polyol ether.

15. The method of claim 12 wherein said polyol or said salt of a polyol comprises glycerol, a sugar alcohol or mixtures thereof.

16. The method of claim 15 wherein said polyol or said salt of a polyol comprises glycerol and said alkylating agent comprises a methylating agent, an ethylating agent or combinations thereof.

17. The method of claim 12 wherein said polyol or said salt of a polyol and said first alkylating agent are reacted in an aqueous solvent.

18. The method of claim 12 wherein said providing and reacting comprise said ketal or acetal of said polyol, and said first alkoxy polyol ether comprises said one or more ketal or acetal moieties and at least one said alkoxy moiety.

19. The method of claim 18 further comprising reacting said first alkoxy polyol ether to hydrolyze said ketal or acetal moieties to additional free hydroxyl moieties, further reacting with a second alkylating agent under conditions effective for alkylation of one or more of the free hydroxyl moieties to produce a second alkoxy polyol ether, and recovering said second alkoxy polyol ether, wherein said second alkylating agent comprises a second alkyl tosylate.

20. The method of claim 19 wherein said first alkyl tosylate is different from said second alkyl tosylate.

21. The method of claim 19 wherein said ketal or acetal of said polyol comprises glycerol, a sugar alcohol or mixtures thereof.

22. The method of claim 21 wherein said ketal or acetal of said polyol comprises glycerol and said first alkyl tosylate and said second alkyl tosylate are independently selected from the group consisting of methyl tosylate and ethyl tosylate.

23. The method of claim 19 wherein said ketal or acetal of said polyol and said first alkylating agent are reacted in an aqueous solvent.

24. A method for producing alkoxy polyol ethers comprising providing a polyol derivative comprising a ketal or acetal of a polyol which comprises at least one free hydroxyl moiety and one or more ketal or acetal moieties, reacting said polyol derivative with a first alkylating agent under conditions effective for alkylation of one or more hydroxyl moieties of said polyol derivative to produce a first alkoxy polyol ether comprising said one or more ketal or acetal moieties and at least one alkoxy moiety and spent first alkylating agent, recovering said spent first alkylating agent and regenerating said spent first alkylating agent.

25. The method of claim 24 further comprising reacting said first alkoxy polyol ether to hydrolyze said ketal or acetal moieties to additional free hydroxyl moieties, further reacting with a second alkylating agent under conditions effective for alkylation of one or more of the free hydroxyl moieties to produce a second alkoxy polyol ether, and recovering said second alkoxy polyol ether, wherein said second alkylating agent comprises a second alkyl tosylate.

26. The method of claim 25 wherein said first alkyl tosylate is different from said second alkyl tosylate.

27. The method of claim 25 wherein said ketal or acetal of said polyol comprises glycerol, a sugar alcohol or mixtures thereof.

28. The method of claim 27 wherein said ketal or acetal of said polyol comprises glycerol and said first alkyl tosylate and said second alkyl tosylate are independently selected from the group consisting of methyl tosylate and ethyl tosylate.

29. The method of claim 25 wherein said ketal or acetal of said polyol and said first alkylating agent are reacted in an aqueous solvent.

30. A method for producing alkoxy polyol ethers comprising providing a polyol derivative comprising a ketal or acetal of a polyol which comprises at least one free hydroxyl moiety and one or more ketal or acetal moieties, reacting said polyol derivative with a first alkylating agent under conditions effective for alkylation of one or more hydroxyl moieties of said polyol derivative to produce a first alkoxy polyol ether comprising said one or more ketal or acetal moieties and at least one alkoxy moiety, reacting said first alkoxy polyol ether to hydrolyze said ketal or acetal moieties to additional free hydroxyl moieties, further reacting with a second alkylating agent under conditions effective for alkylation of one or more of said additional free hydroxyl moieties to produce a second alkoxy polyol ether, and recovering said second alkoxy polyol ether, wherein said first alkylating agent comprises a first alkyl tosylate and said second alkylating agent comprises a second alkyl tosylate, and said first alkyl tosylate is different from said second alkyl tosylate.

* * * * *